United States Patent [19]

Siclari et al.

[11] 4,197,260

[45] Apr. 8, 1980

[54] PROCESS FOR THE PREPARATION OF α,ζDIAMINES AND PRODUCTS OBTAINED THEREFROM

[75] Inventors: Francesco Siclari, Barlassina; Pietro P. Rossi, Garlasco; Mario De Gaetano, Seregno, all of Italy

[73] Assignee: Snia Viscosa, Societa Nazionale Industria Applicazioni Viscosa S.p.A., Italy

[21] Appl. No.: 931,126

[22] Filed: Aug. 4, 1978

Related U.S. Application Data

[63] Continuation of Ser. No. 732,876, Oct. 15, 1976, abandoned.

[30] Foreign Application Priority Data

Oct. 20, 1975 [IT] Italy ............................ 28434 A/75

[51] Int. Cl.$^2$ ............................................. C07C 85/08
[52] U.S. Cl. .................................................. 260/585 C
[58] Field of Search ............ 260/585 C, 583 H, 583 P

[56] References Cited

U.S. PATENT DOCUMENTS 1,966,478   7/1934   Baur ................................ 260/581 X
2,636,051   4/1953   Whetstone et al. ......... 260/585 C X

OTHER PUBLICATIONS

Augustine, "Catalytic Hydrogenation", pp. 57, 102 & 103 (1965).

*Primary Examiner*—John Doll
*Attorney, Agent, or Firm*—McGlew and Tuttle

[57] ABSTRACT

Aliphatic, linear, saturated or unsaturated $\alpha,\omega$-diamines, containing from 8 to 12 carbon atoms, are prepared from the corresponding $\alpha,\omega$-dialdehydes by firstly converting the dialdehyde to di-imine by reaction with ammonia at less than 25° C. and preferably less than 5° C. in a mixture of water and of an organic solvent, and subsequently subjecting the di-imine to reduction with hydrogen in the presence of a catalyst which under the reaction conditions is capable of reducing all the iminic double bonds while leaving any olefinic bonds unchanged. When olefinic bonds are present and it is desired to obtain a saturated diamine, the unsaturated diamine obtained as hereinbefore stated is subjected to hydrogenation in the presence of a catalyst chosen among palladium, platinum, ruthenium and rhodium. Preferred catalysts for the reduction of the di-imine are finely subdivided nickel and cobalt.

19 Claims, No Drawings

PROCESS FOR THE PREPARATION OF α,ζDIAMINES AND PRODUCTS OBTAINED THEREFROM

This is a continuation of application Ser. No. 732,876 filed Oct. 15, 1976, now abandoned.

BACKGROUND OF INVENTION

1. Field of the Invention

This invention refers in general to a process for the preparation of α,ω-diamines.

More particularly, this invention refers to a process for the preparation of aliphatic, linear, saturated or unsaturated α,ω-diamines, containing from 8 to 12 carbon atoms, through the reductive amination of the corresponding α,ω-dialdehydes; saturated dialdehydes yielding saturated diamines and unsaturated dialdehydes yielding either unsaturated or saturated diamines.

2. The Prior Art

The industrial importance of both saturated and unsaturated diamines, is known. To cite some of their main uses, they may serve, as primary components or as additives, in the manufacture of the various types of nylon, of fibers, of elastomers, in the formulation of particular types of alkyd resins, and in the preparation of finishing compositions for textile fibers and of adhesives.

The condensation of diamines with dicarboxylic acids of a suitable molecular weight may yield wetting and emulsifying agents useful in particular in the oil industry.

Further the diamines may be used as hardening agents for epoxy resins.

Various methods for the preparation of higher aliphatic α,ω-diamines are known.

The aliphatic α,ω-diamines may for instance be obtained by the reduction of the corresponding dinitriles, which in turn are obtained from oil derivatives through processes having a very high number of stages.

The numerous attempts to simplify such processes have not been successful.

Thus for instance U.S. Pat. No. 2,657,240 discloses a process whereby diamines may be obtained from cycloolefins ozonides. The preparation of hexamethylenediamine by the ozonization of cyclohexene in alcohol followed by a reductive amination treatment of the ozonide formed, is specifically described.

The yield of the diamine thus obtained is however very low (about 30% with respect to the cyclohexane used). H. Schulz and H. Wagner describe in Angewandte Chemie, 62 (1950) pp. 105-118 a method for the preparation of α,ω-diamines starting from the corresponding dialdehydes, by reductive amination in a single stage.

In particular (pp. 111-117) there is described the preparation of 2-oxy-hexamethylenediamine-b ξ,6 by reductive amination of the corresponding dialdehyde. However this method too is not industrially satisfactory because the yield ot he diamine is only 45-50% and its purity 80-90%.

In view of the importance of the diamine it is obvious that a method affording a higher yield would have great industrial value.

SUMMARY OF THE INVENTION

The applicant has now surprisingly found a process whereby it is possible to prepare with excellent yields and conversion ratios with α,ω-diamines, saturated or unsaturated, by a reductive amination of the α,ω-dialdehydes in two separate stages, in which particular temperature and concentration conditions are observed, the first stage consisting in reacting said dialdehydes with ammonia at low temperature in the presence of a mixture of water and an organic solvent, and the second stage consisting in subjecting the reaction product of the first stage (which for reasons of simplicity will be called hereinafter "di-imine" at a higher temperature to catalytic reduction. Under certain specific preferred reaction conditions hereinafter specified, yields and conversions ratios $\geqq$ of at least 80% may be obtained while avoiding polymerization reactions the aldehyde-ammonia adduct which cause considerable decreases in yield as evidenced by the Tables of Examples 3 to 7B.

It is therefore an object of the present invention to provide a process for the preparation of aliphatic, linear, saturated or unsaturated α,ω-diamines, containing from 8 to 12 carbon atoms, by reductive amination of the corresponding α,ω-dialdehydes, characterized by the fact that the dialdehyde is firstly converted into a di-imine by reaction with ammonia at low temperature in mixture of water and an organic solvent and the di-imine thus obtained is reacted with hydrogen at high temperature in the presence of a catalyst which, under the reaction conditions, is capable of reducing all the iminic double bonds while leaving olefinic bonds unchanged, and finally—if olefinic bonds are present and it is desired to obtain a saturated α,ω-diamine—the unsaturated diamine obtained from the di-imine is subjected to hydrogenation in the presence of a catalyst chosen among palladium, platinum, ruthenium and rodium.

According to the invention therefore, when starting from unsaturated dialdehydes, it is possible to obtain both the corresponding unsaturated diamines and the saturated ones, whereas from saturated dialdehydes only the corresponding saturated diamines can be obtained.

The α,ω-dialdehydes employed as starting material in the process according to the invention, are known compounds or may be prepared, unless otherwise specified, by conventional known methods.

The reaction between the α,ω-dialdehyde and ammonia is preferably effected at a temperature comprised from $-5°$ C. to $+25°$ C. at a pressure from room pressure to 10 Atm. Examples of organic solvents which may be used are alcohols, dioxane and tetrahydrofurane.

The subsequent hydrogenation of the di-imines obtained from said reaction, is preferably effected in the presence of a metal nickel or cobalt catalyst in a finely particulate state in suspension in a suitable solvent, for instance an alcohol such as ethyl alcohol. The hydrogenation is suitably effected at a temperature from 40° to 150° C. under a pressure comprised between 3 Atm. and 80 Atm.

DETAILED DESCRIPTION OF THE PREFERRED EMBODIMENTS

In preferred embodiments of the invention the following conditions are desirably complied with in carrying out the process:

(a) the reaction of the α,ω-dialdehyde with ammonia is effected at a temperature comprised between $-10°$ and $+20°$ C.;

(b) the α,ω-dialdehyde is introduced into the ammonia solution, preferably as a solution;

(c) the molar ratio between the ammonia and the —CHO groups is not less than 5:1;

(d) the solution of the di-imine resulting from the reaction between ammonia and dialdehyde is conveyed to a hydrogenation autoclave wherein a pressure from 25 to 80 Atm. has been already established;

(e) the hydrogenation catalyst is already in suspension in the solvent within the autoclave at a temperature from 80° to 130° C. when the di-imine is charged. The observance of all said critical conditions serves to create an environment in which temperature, pressure and the catalyst are most favourable to the reductive ammination whereby the polymerization of the imine of the unsaturated aldehyde is minimized, the di-imine is charged.

Finely subdivided nickel obtained by decomposition of nickel formate in cyclododecane at 230°–240° C., is the preferred catalyst for the hydrogenation of the di-imine.

According to a more preferred variant of the process according to the invention, the hydrogenation reaction lasts from 15' and 60'.

The $\alpha,\omega$-diamine thus obtained is then isolated and purified by known methods.

When the product is a saturated $\alpha,\omega$-diamine and the starting material is an unsaturated $\alpha,\omega$-dialdehyde, the unsaturated $\alpha,\omega$-diamine obtained by hydrogenation with Ni or Co, is subjected to a further hydrogenation in the presence of a catalyst chosen among palladium, ruthenium, rodium and platinum, said hydrogenation being effected in a conventional way, for instance in the presence of a solvent such as a mixture alcohol-water, dioxane-water, etc., in which the catalyst is suspended, under a pressure from 5 to about 40 Atm. and a temperature from 80° to 140° C.

The saturated diamine thus obtained is subsequently isolated and purified by conventional methods.

The following examples are illustrative and not limitative.

EXAMPLE 1

Preparation of 1,12 Dodecamethylenediamine (A) 48 g. of 1,12-dodecandiale at 98.5% (prepared by reduction at −5° C. with Zn and water of an alcoholic-acetic solution of cyclododecene ozonide obtained in acetic acid and cycloexane) are dissolved in 48 g. of 95% ethyl alcohol, and the solution thus obtained is added, in a closed vessel at −5° C. and under stirring, to a solution consisting of 88.5 g. of ammonia, 50 g. of water and 150 g. of ethyl alcohol; a solution of the di-imine in alcohol is thus obtained.

This solution, maintained at 31 5° C., is conveyed in a period of time of 40' to a stainless steel autoclave maintained under a pressure of 30 Atm. and at a temperature of 120° C., in which autoclave 5 g. of finely subdivided nickel (prepared by decomposition of nickel formate in boiling cyclododecane), 30 g. of ammonia and 50 g. of ethyl alcohol, are already contained. When all the solution has been charged, the reaction is continued under a hydrogen pressure of 35 Atm. for a further 20' at 130° C.

At the end of this period, the autoclave is cooled, the pressure is discharged, and the reaction product is filtered.

By concentration of the filtrate by evaporation of the ammonia, the alcohol and the water, 50.1 g. of a residue are obtained, which residue is distilled under a vacuum.

There are thus obtained 42.6 g. of 1,12-dodecamethylenediamine (having a boiling point of 155° C. at 3.5 mmHg), corresponding to a yield of 90% of theory.

(B) Operating as described hereinbefore under (A), adding however the ammonia to the dialdehyde at −5°, 32.8 g. of 1,12-dodecamethylenediamine are obtained.

EXAMPLE 2

Comparison Example wherein the Di-imine is prepared directly in the Autoclave

In the autoclave of Example 1 there are charged 112.5 g. of ammonia, 200 g. of ethyl alcohol, 5 g. of nickel (prepared from nickel formate as described in Example 1). The solution obtained is cooled to −5°, and 48 g. of 1,12-dodecanediale having a purity of 98.5% (obtained as in Example 1) are added. The autoclave is placed under nitrogen and then heated to 120° C. At this temperature 30 atmospheres of hydrogen are introduced and the reaction is continued for 1 hour.

At the end of this period the reaction is completed during a further 30' until the absorption of hydrogen ceases.

By effecting the treatments described in Example 1 only 28.5 g. of dodecamethylenediamine are obtained after distillation. This example shows that if the di-imine solution is not introduced when cold into an environment in which the most favourable reaction conditions already exist, but is brought to such conditions through gradual stages which already are more or less slow and unfavourable, the diammine yields decrease considerably.

CONTROL EXAMPLES 7A AND 7B

These examples prove the fundamental importance of the temperature in the preparation of the di-imine for the achievement of good diammine yields. If the preparation of the di-imine by addition of the aldehyde in hydro-alcoholic solution to ammonia in hydro-alcoholic solution is effected at a temperature of 25° C. or higher, an insoluble polymer is formed which is no longer adapted to furnish appreciable amounts of di-imine by reductive amination with hydrogen and catalyst.

In Example 7A, the operations of Example 1 have been repeated using aqueous ethyl alcohol as the solvent of the aldehyde and the ammonia. To be able to maintain at 25° C. a 10:1 NH₃/CHO ratio, as was desired, the ammonia has been introduced into the aqueous solution in gaseous form at a pressure sufficient to keep all the ammonia in solution. The aldehyde dissolved in ethyl alcohol has been introduced thereafter into the apparatus for the preparation of aqueous-alcoholic ammonia solution, under efficient agitation, by means of a piston pump in order to overcome the pressure which existed in the vessel. After some moments from the end of said introduction, the formation of a white polymer was noted, which was insoluble in the aqueous-alcoholic ammonia solution and which remained dispersed in the liquid due to the agitation. This dispersion has been then conveyed into the reductive ammination autoclave. By operating as described in Example 1, about 1 gr. of dodecamethylenediammine was obtained and the yield was therefore less than 5%. Further, the separation of the diammine was difficult because of the presence of the polymer which remained insoluble and therefore dispersed in the mass even after treatments with hydrogen and catalyst.

In Example 7B, the operations of Example 1 have been repeated with a 10:1 $NH_3/CHO$ ratio but at di-imine formation temperature of 5° C. The yield of dodecamethylenediammine, in this case, was about 60%.

The conditions and yields of Examples 3 to 7 and control Examples 7A and 7B, are tabulated in the following Table:

| Example n° | Solvent | Preparation of the di-imine | | Yield of dodeca-methylenediamine % |
|---|---|---|---|---|
| | | Molar ratio $NH_3/CHO$ | Temp. 0° C. | |
| 3 | Ethyl alcohol + $H_2O$ | 10/1 | −10 | 86.5 |
| 4 | Ethyl alcohol + $H_2O$ | 5/1 | −10 | 80.3 |
| 5 | Dioxane + $H_2O$ | 10/1 | −15 | 87.1 |
| 6 | Tetrahydro furane + $H_2O$ | 10/1 | −5 | 85.4 |
| 7 | Ethyl alcohol + $H_2O$ | 2/1 | −10 | 48.4 |
| 7A | Ethyl alcohol + $H_2O$ | 10/1 | +25 | 5 (polymerization of the di-imine) |
| 7B | Ethyl alcohol + $H_2O$ | 10/1 | +5 | about 60% |

Example 7 is also a control example which indicates the importance of the ratio $NH_3/CHO$ and of the temperature of the formation and conversation of the di-imine.

From the Table it is noted that changing the nature of the solvent does not greatly affect the yield, whereas the molar ratio of ammonia to the aldehyde groups is decisive.

EXAMPLE 8

Preparation of 1,8-Octamethylenediamine 30 g of suberaldehyde 97.5% pure (obtained from cyclooctadiene monoozonide by reduction thereof with zinc in powder at −5° C.), are dissolved in 30 cc. of ethyl alcohol and the solution obtained is added at 0° C. to a solution consisting of 60 g. of ammonia, 30 g. of $H_2O$ and 100 g. of ethyl alcohol, contained in a closed vessel. 5 g. of nickel (obtained from nickel formate), 30 g. of ammonia and 50 g. of ethyl alcohol are separately introduced in the autoclave described in Example 1; the temperature of the autoclave is then brought to 130° C. and the pressure to 40 atmospheres with hydrogen. The solution of the di-imine of the suberaldehyde thus obtained is then pumped into the autoclave during 35', the reaction is completed at the same temperature and pressure during another 15' and then, after discharge, filtration of the catalyst and evaporation of the solvents, the residual diamine is distilled under a vacuum.

23.8 g. of 1,8-octamethylenediamine (boiling point at 15 mmHg=115°−118° C.), corresponding to a yield of 80%, are thus obtained.

The 1,10-decamethylenediamine (boiling point at 35 mmHg=119.2°) is prepared similarly to what described hereinbefore, employing however, in place of the suberaldehyde, 36.4 g. of 96.2% pure sebacic dialdehyde.

EXAMPLE 9

Preparation of 1,12-Diaminododeca-4,8-Diene 44 g. of dodeca-4,8-diene-1,12-diale (boiling point at 0.1 mmHg=116°−120° C.), prepared by the reduction with zinc at −5° C. of cyclododecatriene monoozonide obtained by ozonization of cyclododecatriene in cyclo-exane and acetic acid, are treated with an alcoholic ammonia solution, and the di-imine obtained is hydrogenated as described in Example 1.

The product obtained from the hydrogenation, after the filtration of the catalyst and the evaporation of the solvents, consists of 1,12-diaminododeca-4,8-diene. Said compound is isolated by known methods, for instance by dissolving in toluene, treating with $CO_2$, filtering the white precipitate (43.5 g) constituted by diamine carbamate, drying at a low temperature and heating under a vacuum to decompose the carbamate.

34.1 g. of 1,12-diaminododeca-4,8-diene (boiling point at 0.3 mmHg=128°−130° C.) are thus obtained.

EXAMPLE 10

Preparation of 1,10-Diamino-4-Decene

For the preparation of 1,10-diamino-4-decene, the 4-decene-1,10-diale obtained by the reduction of cyclodode cadiene monoozonide according to the method specified in Example 9, is employed.

By following the same procedure for the reductive amination and the separation of the product described in Example, 9, 1,10-diamino-4-decene (boiling point at 0.3 mmHg =108°−111° C.) is obtained after heating under a vacuum. The yield is 82.3%.

In the same way, from the unsaturated dialdehyde 4-ocetene-1,8-diale the corresponding unsaturated diamine is obtained, which is 1,8-diamino-4-ocetene (Boiling point at 0.3 mmHg=95°−98° C.), The yield is 78.4%.

We claim:

1. Process for the preparation of aliphatic, linear, saturated or unsaturated α,ω-diamines, containing from 8 to 12 carbon atoms, which comprises subjecting α,ω-dialdehyde corresponding to said α,ω-diamines to reductive amination in the liquid phase of said α,ω-dialdehyde, said reductive amination being carried out in two stages wherein, (a) in a first, non-catalytic stage said α,ω-dialdehyde is converted to di-imine by reaction at a temperature less than about 25° C. with ammonia in a mixture of water and an organic solvent, and (b) in a second stage, the product di-imine thus obtained from (a) is subsequently subjected to reduction with hydrogen by feeding said product to a reaction vessel containing a suspension of a catalyst in a hydrogenation solvent under a pressure of from about 25 to about 80 atm and a temperature of from about 80° C. to about 135° C., said catalyst under the reaction conditions being capable of reducing all the iminic double bonds while leaving unchanged any olefinic bonds.

2. Process according to claim 1, wherein the olefinic bonds in the product of stage two are subjected in a third stage (c) to hydrogenation in the presence of a catalyst selected from the group consisting of palladium, ruthenium and rhodium.

3. Process according to claim 1, wherein the temperature of the reaction in the first stage is less than 5° C.

4. Process for the preparation of aliphatic, linear, saturated α,ω-diamines, containing from 8 to 12 carbon atoms by reductive amination in the liquid phase of the corresponding saturated α,ω-dialdehydes which comprises the steps: (a) in a first stage, converting a saturated linear aliphatic α,ω-dialdehyde having 8 to 12 carbon atoms to a di-imine by reacting said dialdehyde with ammonia at a temperature less than about 25° C. in the absence of a catalyst in a mixture of water and an organic solvent, and (b) in a second stage, hydrogenating said di-imine thus obtained to produce a diamine by feeding it to a reaction vessel containing a suspension of a catalyst in a hydrogenation solvent under a pressure of from about 25 to 80 atm and a temperature of from about 80° C. to 135° C., said catalyst being able under the reaction conditions of reducing all the imine double bonds.

5. Process according to claim 4, wherein the molar ratio of the ammonia to aldehyde groups in (a) is not less than about 5:1.

6. Process according to claim 4, wherein the reaction of the dialdehyde with ammonia in (a) is effected at a temperature of crom about −10° C. to about 20° C., and the dialdehyde is added to the ammonia solution.

7. Process according to claim 4, wherein the organic solvent is a member selected from the group consisting of alcohols, dioxane and tetrahydrofurane.

8. Process according to claim 4, wherein said catalyst in (b) for the hydrogenation of the di-imine from (a) comprises a finely divided metallic catalyst selected from the group consisting of nickel and cobalt, and said catalyst is suspended in an alcohol.

9. Process according to claim 8, wherein said catalyst consists essentially of finely divided nickel prepared by decomposition of nickel formate in cyclododecane at 230°–240° C. and said alcohol consists essentially of ethyl alcohol.

10. Process for the preparation of aliphatic, linear, unsaturated $\alpha,\omega$-diamines containing from 8 to 12 carbon atoms by reductive amination of the corresponding unsaturated $\alpha,\omega$-dialdehydes, which comprises converting an unsaturated linear aliphatic $\alpha,\omega$-dialdehyde having 8 to 12 carbon atoms in two stages to an unsaturated di-imine; in a first stage (a) reacting said dialdehyde with ammonia at a temoerature less than 25° C. in the absence of a catalyst in a mixture of water and an organic solvent, and (b) in a second stage hydrogenating the di-imine thus obtained from (a) to produce an unsaturated diamine in the presence of a catalyst which under the reaction conditions is capable of reducing all the iminic double bonds while leaving unchanged any olefinic bonds.

11. Process according to claim 10, wherein the molar ratio between ammonia and the aldehyde groups is not less than 5:1.

12. Process according to claim 11, wherein the reaction of the dialdehyde with ammonia is effected at a temperature of from about −10° to +20° C., the dialdehyde being added to the ammonia solution.

13. Process according to claim 10, wherein the organic solvent is selected from the group consisting of an alcohol, dioxane and temohydrofurane.

14. Process according to claim 10, wherein the hydrogenation of the di-imine is effected by feeding said di-imine to a reaction vessel containing a suspension of the hydrogenation catalyst in a hydrogenation solvent, at a hydrogenation temperature of from 80° to 135° C. and hydrogenation pressure of from 25–80 atm.

15. Process according to claim 14, wherein said catalyst consists essentially of a finely subdivided metallic catalyst selected from the group consisting of nickel and cobalt and said solvent consists essentially of an alcohol.

16. Process according to claim 15, wherein said catalyst consists essentially of nickel prepared by decomposition of nickel formate in a cyclododecane at a temperature in the range of 230°–240° C. and said alcohol consists essentially of ethyl alcohol.

17. Process according to claim 10, wherein said unsaturated diamine so-produced is subjected to a further stage of hydrogenation in the presence of a metal catalyst selected from the group consisting of palladium, ruthenium and rhodium, whereby the corresponding saturated diamine is produced.

18. Process for the preparation of aliphatic, linear, $\alpha,\omega$-diamines, containing from 8 to 12 carbon atoms, by reductive amination in the liquid phase of the corresponding $\alpha,\omega$-dialdehydes, which comprises converting the corresponding dialdehyde to di-imine (a) in a first noncatalytic stage by reacting said $\alpha,\omega$-dialdehyde with ammonia at a temperature of from about −10° C. to about +20° C. in a solvent mixture containing water and an organic solvent selected from the group consisting of alcohol, dioxane and tetrahydrofurane, the molar ratio of ammonia to —CHO groups being not less than 5:1; and subsequently (b) in a second catalytic stage subjecting the so-obtained di-imine to reduction with hydrogen under a pressure of between about 25 atm to 80 atm at a temperature of between 80° C. to 135° C. in the presence of a finely subdivided metallic catalyst, which is capable, under the reaction conditions, of reducing all the imine double bonds, while leaving unchanged any olefinic bonds, said catalyst being selected from the group consisting of nickel and cobalt, and being in suspension in a hydrogenation solvent and in the case in which olefinic bonds are present and it is desired to obtain a saturated $\alpha,\omega$-diamine, the unsaturated di-imine obtained as aforesaid is subjected in a third stage to hydrogenation under a pressure of from about 5 to 40 atm at a temperature from about 80° C. to 140° C. and in the presence of a catalyst selected from the group consisting of palladium, ruthenium and rhodium.

19. Process according to claim 18, wherein said catalyst for the hydrogenation of di-imine to di-imine comprises a finely divided nickel catalyst prepared by the decomposition of nickel formate in cyclododecane at a temperature of from 230° to 240° C. and said catalyst is suspended in ethyl alcohol.

* * * * *